| (12) | United States Patent<br>Wang et al. | (10) Patent No.: US 10,519,484 B2<br>(45) Date of Patent: Dec. 31, 2019 |
|---|---|---|

(54) LYTIC COMPOSITION AND APPLICATION THEREOF, KIT, METHOD FOR PREPARING NUCLEIC ACID BY UTILIZING LYTIC COMPOSITION, AND NUCLEIC ACID ANALYSIS METHOD

(71) Applicants: Xiaohui Wang, Shanghai (CN); Health&Help Bioscience Co., LTD, Shanghai (CN)

(72) Inventors: Xiaohui Wang, Shanghai (CN); Dongjie Sun, Shanghai (CN); Qingqing Zhuang, Shanghai (CN); Lihan Jiang, Shanghai (CN); La Sa, Shanghai (CN)

(73) Assignees: Xiaohui Wang, Shanghai (CN); HEALTH & HELP BIOSCIENCE CO., LTD, Shanghai (CN)

( * ) Notice: Subject to any disclaimer, the term of this patent is extended or adjusted under 35 U.S.C. 154(b) by 81 days.

(21) Appl. No.: 15/472,510

(22) Filed: Mar. 29, 2017

(65) Prior Publication Data

US 2017/0283856 A1 Oct. 5, 2017

Related U.S. Application Data

(63) Continuation of application No. PCT/CN2015/087573, filed on Aug. 20, 2015.

(30) Foreign Application Priority Data

Sep. 30, 2014 (CN) .......................... 2014 1 0522821

(51) Int. Cl.
*C12Q 1/68* (2018.01)
*C12Q 1/6806* (2018.01)
*C12N 15/10* (2006.01)
*G01N 1/28* (2006.01)

(52) U.S. Cl.
CPC ............ *C12Q 1/6806* (2013.01); *C12N 15/10* (2013.01); *C12N 15/1003* (2013.01); *G01N 1/28* (2013.01)

(58) Field of Classification Search
CPC ..................................................... C12N 15/10
USPC ........................................ 536/25.41; 435/6.1
See application file for complete search history.

(56) References Cited

U.S. PATENT DOCUMENTS

2006/0147944 A1\* 7/2006 Chomczynski ...... C12Q 1/6806
435/6.18

\* cited by examiner

*Primary Examiner* — Jezia Riley
(74) *Attorney, Agent, or Firm* — HYIP

(57) ABSTRACT

The present invention relates to the technical field of biology, and in particular relates to a lytic composition and an application thereof, a kit, a method for preparing nucleic acid by utilizing the lytic composition, and a nucleic acid analysis method. A lytic product obtained in the present invention can be directly used for the nucleic acid analysis method without purifying the nucleic acid. According to the lytic composition disclosed by the present invention, multiple biological tissues and cells are lysed so as to release the nucleic acid of the cells into a solution, the nucleic acid in a whole-cell lysing and mixing state directly serves as a template without using a conventional nucleic acid separation and purification process after termination of the reaction, and nucleic acid amplification analysis is guided. For example, nucleic acid amplification is performed by a real-time fluorescence qPCR, etc.

11 Claims, 10 Drawing Sheets

Specification includes a Sequence Listing.

LYTIC COMPOSITION AND APPLICATION THEREOF, KIT, METHOD FOR PREPARING NUCLEIC ACID BY UTILIZING LYTIC COMPOSITION, AND NUCLEIC ACID ANALYSIS METHOD

TECHNICAL FIELD

The present invention relates to the technical field of biology, and in particular relates to a lytic composition and application thereof, a kit, a method for preparing nucleic acid by utilizing the lytic composition, and a nucleic acid analysis method.

BACKGROUND OF THE INVENTION

Fluorescent quantitative polymerase chain reaction (qPCR) is a DNA amplification technology improved in multiple aspects based on a polymerase chain reaction (PCR). When the qPCR is performed in a thermal cycler instrument, the instrument illuminates each DNA sample by emitting light beams of special wavelengths and detects and excites fluorescence emitted by fluorophonre. qPCR needs to use a fluorescent probe or fluorescent primers, and the variation quantity of target DNA can be monitored by a real-time PCR instrument during instant amplification. In addition, the qPCR is further capable of simultaneously amplifying one or more target DNA sequences.

The quantitative PCR has strict requirements for DNA templates, and can be performed by purifying pure DNA from biological samples generally. The conventional complicated DNA extraction methods are mainly as follows: (1) a classical conventional phenol/chloroform DNA extraction method is time-consuming, complicated in extraction steps and high in toxicity and cannot be used for a high-throughput experiment. In addition, chemical phenol/chloroform reagents have been demonstrated to be important cancerogenic substances in labs, being able to cause irreversible injuries to the body of an operator due to long-term exposure and may form a large threat to health and safety; (2) in an ion exchange spin column method, DNA is collected by a silica membrane, the multi-steps are relatively complicated, a centrifugal machine needs to be repeatedly used, centrifuge tubes are repeatedly replaced, DNA contamination among samples may occur, DNA is easily lost in the experimental process, the extraction amount is small, the price is high, and lab wastes which are difficult to eliminate may be produced. The above two methods are not favorable for the high-throughput experiment; and (3) a magnet bead method (also known as a glass bead separation method): the method for purifying DNA by using magnet beads is relatively simple and convenient, and the frequency of replacing the centrifuge tubes is relatively low, while multiple steps are needed, and a high-value expensive special equipment of an automatic workstation is needed. The automatic workstation adopted in the DNA purification method by magnet beads is very typical high-value equipment. DNA is also partially lost in the experimental process. In addition, although the frequency of replacing the centrifuge tubes is relatively low in the DNA separation method by magnet beads, multiple steps are needed, and expensive special equipment is needed. In these existing technologies, the centrifuge tubes need to be repeatedly replaced or the DNA needs to be repeatedly cleaned and collected, thereby easily causing cross contamination of samples. There is limited report about methods for directly performing real-time quantitative PCR without DNA extraction, especially for use of many kinds of samples. Therefore, the provision of a lytic composition which can be directly used for nucleic acid analysis without nucleic acid purification, a kit, a method for preparing nucleic acid by utilizing the lytic composition and a nucleic acid analysis method has great practical significances.

SUMMARY OF THE INVENTION

In view of this, the present invention provides a lytic composition and an application thereof, a kit, a method for preparing nucleic acid by utilizing the lytic composition, and a nucleic acid analysis method. The lytic composition is capable of rapidly and simply preparing the nucleic acid to be directly used for nucleic acid analysis.

In order to achieve the above purpose of the present invention, the present invention provides the following technical solution:

The present invention provides a lytic composition, including A and B, or a combination of A and B.

A is selected from NaOH, KOH or $Ca(OH)_2$; and B is PEG

PEG, i.e., polyethylene glycol, is also known aspolyethylene oxide (PEO) or polyoxyethylene (POE), and refers to an oligomer or a polymer of ethylene oxide. The three names are generally synonyms nowadays, while in history, the PEG often refers to oligomers and polymers with molecular mass of lower than 20000 g/mol, PEO refers to polymers of which the molecular weight exceeds 20000, and POE may refer to polymers of any molecular mass. The PEO and POE may be liquid or low-melting-point liquid according to different molecular weights. Due to the influence of chain lengths, PEGs of different molecular weights often have different physical properties (such as viscosity) and different applications. Preferably, the molecular weight of PEG is 100-2000.

In some embodiments of the present invention, the concentration of A in the lytic composition is 0.1-200 mmol/L, and the concentration of B is 1-200 mg/mL.

In some embodiments of the present invention, the lytic composition further includes a reaction termination product. In some embodiments of the present invention, the reaction termination product may be a substance capable of terminating a lytic reaction. Preferably, the reaction termination product is Turbo Buffer. Any reagent capable of terminating the lytic reaction of biological samples can be used, and is not limited in the present invention.

In some embodiments of the present invention, a molar ratio of A to B is (0.1-200):(0.45-1.05) when the lytic composition includes A and B.

The present invention further provides an application of the lytic composition above in preparation of nucleic acid by lysing biological samples.

In some embodiments of the present invention, a mass-volume ratio of the biological samples to the lytic composition is (1-1):(1-10) (based on g/mL).

In some embodiments of the present invention, the biological samples include humans.

In some embodiments of the present invention, the eukaryotes include the humans.

In some embodiments of the present invention, the humans include fluid tissues and animal solid tissues.

In some embodiments of the present invention, the human fluid tissues include one or a mixture of more than two of saliva, sputum, throat fluid, esophagus (sputum) fluid, urine, blood, gastric juice, hydrothorax, pulmonary edema, hydrohepatosis, abdominal dropsy, vaginal discharge fluid, uterine drain fluid, sweat, parotid gland cells, lymph, marrow fluid, milk, tears, seminal fluid, spinal fluid, brain marrow, amniotic fluid, synovial fluid, nasal discharge or nasal excrements.

In some embodiments of the present invention, the human solid tissues include one or a mixture of more than two of intestinal tissues, throat tissues, esophageal tissues, bladder tissues, abdominal tissues, tumor tissues, cell lines, lung tissues, hepatic tissues, gastric tissues, nephridial tissues, pancreatic tissues, prostate tissues, uterus tissues, vaginal tissues, ovarian tissues, gall tissues, heart tissues, dermal tissues, brain, tumors, fingernails, hair on the human head, hair on the human body and head, hair follicles, intestinal excretion tissues or excrements.

In the present invention, the prepared nucleic acid can be directly used for nucleic acid analysis without purification.

In some embodiments of the present invention, the nucleic acid analysis includes an amplified reaction, mutant site detection or SNPs detection.

In some embodiments of the present invention, the nucleic acid analysis refers to qPCR, a ligase-chain reaction (LCR), a gap-LCR, a repaired chain reaction, transcription-mediated amplification, autonomous sequence replication, selective amplification of target polynucleotide series, a consensus sequence primer PCR, a random primer PCR, nucleic acid sequence based amplification, strand displacement amplification, loop-mediated isothermal amplification, DNA methylation, a reverse transcription reaction, a DNA ligation reaction and a nuclease-mediated reaction.

In some other embodiments of the present invention, the qPCR includes the conventional qPCR and RT-qPCR (RNA).

In some other embodiments of the present invention, the reverse transcription reaction includes ordinary RNA reverse transcription, RNAi reverse transcription, SiRNA, LncRNA or miRNA reverse transcription.

The present invention further provides a kit, including the lytic composition above. In some embodiments of the present invention, in the kit provided by the present invention, the molar ratio of A to B is (0.1-200):(0.45-1.05) when the lytic composition includes A and B.

The present invention further provides an application of the kit used for preparing nucleic acid by lysing biological samples.

In some embodiments of the present invention, a mass-volume ratio of the biological samples to the lytic composition in the kit is (1-1):(1-10) (based on g/mL).

In some embodiments of the present invention, the nucleic acid prepared by lysing the biological samples by utilizing the kit can be directly used for nucleic acid analysis without purification.

In some embodiments of the present invention, the nucleic acid analysis includes the amplified reaction, mutant site detection or SNPs detection.

In some embodiments of the present invention, the nucleic acid analysis refers to the qPCR, the ligase-chain reaction (LCR), the gap-LCR, the repaired chain reaction, the transcription-mediated amplification, the autonomous sequence replication, the selective amplification of target polynucleotide series, the consensus sequence primer PCR, the random primer PCR, the nucleic acid sequence based amplification, the strand displacement amplification, the loop-mediated isothermal amplification, the DNA methylation, the reverse transcription reaction, the DNA ligation reaction and the nuclease-mediated reaction.

In some other embodiments of the present invention, the qPCR includes the conventional qPCR and RT-qPCR (RNA).

In some other embodiments of the present invention, the reverse transcription reaction includes ordinary RNA reverse transcription, RNAi reverse transcription or miRNA reverse transcription.

The present invention further provides a method for preparing nucleic acid, including a step of lysing biological samples to prepare the nucleic acid by utilizing the lytic composition above.

The present invention further provides a nucleic acid analysis method, wherein the nucleic acid is prepared by lysing the biological samples by using the lytic composition above, and can be directly used for nucleic acid analysis without purification.

Specifically, a process for sequentially performing tissue lysis and nucleic acid analysis by using the lytic composition includes the following steps:
1. adding biological samples such as tissues, cells, etc. into the lytic composition provided by the present invention, wherein the mass-volume ratio of the biological samples to the lytic composition is (1-1):(1-10) (based on g/mL);
2. treating for 10 minutes to 8 hours at a high temperature of 30-90° C.;
3. adding Turbo buffer (Shanghai Honghui Health Science and Technology Co., Ltd.) after lysis, and terminating the reaction; and,
4. centrifuging and then performing nucleic acid analysis.

Multiple human tissues and cells are treated by a novel lytic composition in the present invention, so that nucleic acid is efficiently released from the biological samples and does not need to be extracted, and the operation is completed in two steps in a centrifuge tube so as to directly provide a template for nucleic acid analysis, thereby replacing a conventional method for performing nucleic acid analysis by lysing the cells to extract template nucleic acid.

Specifically, a process for sequentially performing tissue lysis and carrying out a qPCR by using the lytic composition in the present invention includes the following steps:
1. adding the biological samples such as the tissues, the cells, etc. into the lytic composition provided by the present invention, wherein the mass-volume ratio of the biological samples to the lytic composition is (1-1):(1-10) (based on g/mL);
2. treating for 10 minutes to 8 hours at a high temperature of 30-90° C.;
3. adding Turbo buffer (Shanghai Honghui Health Science and Technology Co., Ltd.) after lysis, and terminating the reaction; and,
4. centrifuging and then carrying out the qPCR.

In some embodiments of the present invention, the nucleic acid prepared by the conventional method serves as a control group, and the nucleic acid prepared by the lytic composition provided by the present invention serves as an experimental group; it is discovered that the nucleic acid prepared by the lytic composition provided by the present invention can directly provide a template for nucleic acid analysis without extraction, and there is no obvious difference (P is more than 0.05) between an effect of the experimental group and an effect of the control group.

The present invention provides the lytic composition and an application thereof, the kit, the method for preparing nucleic acid by utilizing the lytic composition, and the nucleic acid analysis method. The lytic composition is capable of rapidly and simply preparing the nucleic acid to be directly used for nucleic acid analysis.

The present invention provides a novel lytic composition, and multiple human and other biological tissues and cells are lysed by the lytic composition, so that the nucleic acid is efficiently released from the cells and does not need to be extracted, and the operation is completed in two steps in a centrifuge tube so as to directly provide the template for the nucleic acid analysis, thereby replacing the conventional method for performing nucleic acid analysis by lysing the cells to extract template nucleic acid.

A very simple nucleic-acid-purification-free, one-step lysis procedure is adopted in the present invention, thereby obviously saving time, reducing cost of labor and consumables, and more importantly, reducing cross contamination of samples as well as infections of the samples to operators, without losses of nucleic acid samples (particularly for low-copy/trace of special samples, such as early disease cell tissues). The technical method has obvious characteristics of being rapid, convenient and favorable for high-throughput and high-sensitivity biological sample analysis. In addition, the method avoids the use of toxic cancerogenic substances and is favorable for health and environment friendliness, fewer in steps, simple in process, low in time consumption, convenient, suitable for large numbers of samples, efficient, fewer in wastes and environmental-friendly (absence of cancerogenic substances, low consumables and fewer wastes), and preparation samples are added in one tube only (for reducing contamination). The nucleic acid is not lost, and trace sample detection is facilitated.

Figure 10:
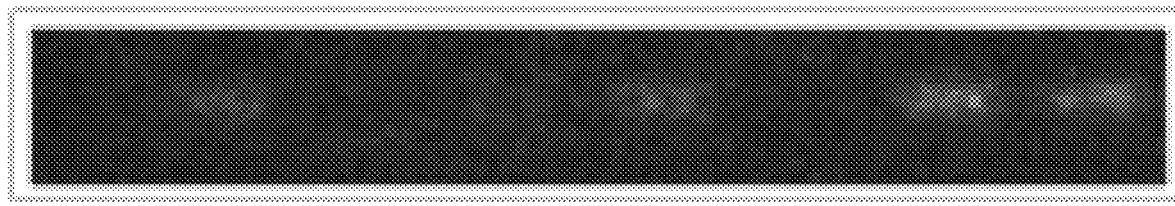

Remarks: gDNA (human genome DNA) refers to human genome DNA (gDNA, the product of Roche) purified and extracted by the conventional method, serving as the DNA template; in all the experiments of this article, the gDNA serves as the positive control so as to compare with positive control without extracting DNA by the method;

FIG. 10 is an amplified electrophoretogram illustrating extraction-free DNA prepared by the lytic composition to be directly used for ordinary qPCR, but qualitively versulized by running a gel, instead of quantitatively analyzed by the qPCR machine automatically (about 110 base pairs amplified fragments), wherein a lane 1 refers to NTC (template-free control) result: −; a lane 2 refers to 20 ng gDNA (human genome DNA control) result: +; a lane 3 refers to blood (lysate-free) result: −; a lane 4 refers to blood (+lysate) result: +; a lane 5 refers to blood (+lysate+Turbo buffer)+; a lane 6 refers to esophagus (lysate-free) result: −; a lane 7 refers to esophagus (+lysate) result: +; and a lane 8 refers to esophagus (+lysate+Turbo buffer) result: +.

DETAILED DESCRIPTION OF THE INVENTION

The present invention discloses a lytic composition and an application thereof, a kit, a method for preparing nucleic acid by utilizing the lytic composition, and a nucleic acid analysis method. Those skilled in the art may appropriately modify technical parameters with reference to the contents in this article. It should be specifically noted that, all similar replacements and modifications are apparent to those skilled in the art, and are considered to be included in the present invention. The method and application provided by the present invention have been described by preferred embodiments, and those skilled in the art apparently can modify or appropriately change and combine the method and application in the article without deviating from the contents, spirit and scope of the present invention, thereby realizing and applying the technology in the present invention.

Raw materials and reagents used in the lytic composition and the application thereof, the kit, the method for preparing nucleic acid by utilizing the lytic composition, and the nucleic acid analysis method provided by the present invention may be purchased from the market, wherein Turbo Buffer is purchased from Shanghai Honghui Health Science and Technology Co., Ltd.

Explanation of Terms

Nucleic acid: referring to a double-stranded or single-stranded deoxyribonucleic acid or ribonucleic acid polymer (DNA and RNA).

DNA: deoxyribonucleic acid, a carrier of biological genetic information, various combinations of deoxyribonucleotide containing four kinds of bases, that is, ATCG, that forms genetic information with high significance.

RNA: ribonucleic acid is composed of ribonucleotide (containing four kinds of bases, that is, AUCG). RNA is an intermediate carrier of genetic information of organisms with cells structures for guiding protein synthesis, also participates in regulation of gene expression, and is also a genetic material of partial viruses.

Cell Lysis and DNA Extraction:

Cell membranes and cell walls of biological samples are disrupted by cell lysis under ordinary conditions, so that DNA, proteins and other materials in cells are released; then impurities are removed by using multiple methods (e.g., use of SDS and protease K), and nucleic acid in the samples is partially purified[such as extracted and purified by hydroxylbenzene (also called phenol) and chloroform, and precipitated by ethanol]. Generally only the purified DNA can be used for a reaction template with high technical requirements and high quality.

PCR (Polymerase Chain Reaction): a (classical) polymerase chain reaction, a molecular biological technique, carried out by taking DNA as a template, and replicating regions with amplification needs by using DNA polymerase. PCR is one of the most useful methods used for nucleic acid amplification, and on the basis, many variations are derived to be applied to different purposes, such as real-time quantitative nucleic acid amplification, namely qPCR.

A full English name of qPCR (q-PCR, Quantitative PCR) is Real-time Quantitative PCR Detecting System, that is, a real-time fluorescent quantitative nucleic acid amplification detecting system, also called a real-time quantitative gene amplification fluorescence detection system, short for qPCR, quantitative PCR. A real-time quantitative qPCR instrument and real-time fluorescent quantitative reagents form qPCR-DNA/RNA real-time fluorescent quantitative detection. Real-time fluorescent qPCR is to continuously detect change of a fluorescence value of each sample at every moment of amplification.

Real-time qPCR is an accurate, effective and rapid nucleic acid detection method. The technology of the method is to take DNA as a template for completing real-time DNA amplification change analysis by using the fluorescent quantitative qPCR instrument. The real-time qPCR is based on the traditional polymerase chain reaction (PCR), but is improved as follows: 1) a real-time qPCR method is used for quantitatively detecting amplification products by fluorescence; 2) combined nucleic acid amplification and detection are simultaneously performed in one step; 3) PCR post-amplification is avoided; 4) usage of sample materials is less than that of the traditional PCR, and the real-time qPCR is more sensitive. Therefore, the technology realizes a leap of qualitative PCR to quantitative PCR, and compared with the conventional PCR, the real-time qPCR has the characteristics of high specificity, capacity of effectively solving PCR contamination, high degree of automation, etc. Since the real-time fluorescent quantitative qPCR (Real-time qPCR) technology was introduced by American Applied Biosystems (ABI) company in 1996, applications of the technology have been very wide at present, such as application in the most advanced clinical nuclear acid molecular diagnosis of diseases. At present, many molecular detection kits for serious diseases have been approved by FDA of America and many other countries, and licensed in clinical applications.

The qPCR technology is widely applied to the fields of rapid and accurate molecular detection of genes and nucleic acid (DNA and RNA), such as detection of DNA molecules of human diseases, molecular mutations of diseases, as well as assistance on advanced individual medical plan making; and the qPCR method can be further used for rapidly detecting gene polymorphisms of organisms, disease susceptibility and individual medical plans. The technology has similar applications in other organisms.

The present invention is applied to the fields of biotechnology research and development, individualized medical treatment and health (hospitals, diagnostic centers and health centers), individualized medicine research and development, health care, food inspection, teaching and environment friendliness.

Direct qPCR or other direct enzyme reactions: by using this expression, the biological samples are directly used for carrying out a specific enzymic catalytic reaction by a mixture subjected to cell lysis, without the conventional multi-step nucleic acid separation or purification in advance. Enzyme inhibitors contained in the biological samples may be artificially added for achieving a certain purpose, such as a stabilizing effect. For example, the blood is one of the samples containing the most enzyme inhibitors. The conventional nucleic acid separation or purification aims to remove or prevent the effects of the enzyme inhibitors. The method provided by the present invention is capable of not only successfully lysing the cells, but also preventing or reducing an effect of inhibiting a subsequent specific nuclease reaction in the absence of separation and purification steps.

The terms such as "nucleic acid" and "nucleotide sequence" used in the article may refer to nucleic acid materials themselves, and are not limited to biochemical definition of specific nucleic acid, such as sequence information of DNA or RNA molecules (letter combinations of five base letters such as ACGT or ACGU).

The terms such as "nucleic acid amplification" or "amplification sequence" used in the article refer to various linearly or exponentially increased technologies of DNA or RNA sequences, and may be products of amplified reactions. The amplified reactions include reactions under thermal cycle or isothermal conditions. The sequence may be single-stranded or double-stranded or divided strands separated by the later. The amplification technologies in the embodiments include but are not limited to qPCR or any other technology utilizing a primer extension sequence. Other non-restricted examples of amplification include but are not limited to the followings:

"Amplified reaction" refers to a reaction used for amplifying nucleic acid molecules, includes but is not limited to the polymerase chain reactions: qPCR, reverse transcriptase reactions (RT-PCR, RNAi, RNA, SiRNA amplification), the LCR, the gap-LCR, the repaired chain reaction, the transcription-mediated amplification (TMA), the autonomous sequence replication, the selective amplification of target polynucleotide series, the consensus sequence primer PCR (CP-qPCR), the random primer PCR (AP-qPCR), the nucleic acid sequence based amplification (NASBA), the strand displacement amplification and the loop-mediated isothermal amplification (LAMP). In addition, there are other amplification technologies.

Enzyme reaction inhibitor: multiple qPCR polymerase reaction inhibitors exist in the biological samples, such as deoxyribonuclease, protease, cholate, $K^+$ and $Na^+$ salts, etc., and the blood also contains hemoglobin and immunoglobulin. Moreover, anticoagulants, such as heparin, sodium citrate or EDTA, added when a blood sample is used, may influence DNA qPCR amplification.

The present invention is further described below by combining the embodiments:

Remarks: gDNA (human genome DNA) refers to the human genome DNA (gDNA, the product of Roche company) purified and extracted by the conventional method, serving as the human DNA template; in all the experiments of this article, the gDNA serves as the positive control so as to compare with the other positive control without extracting DNA by the method Embodiment 1 Preparation of Lytic Composition Component A: NaOH with the concentration of 200 mmol/L;
component B: PEG (with molecular weight of 2000) with the concentration of 1 mg/mL;
a molar ratio of A to B is: 150:0.75;
the lytic composition is prepared.

Embodiment 2 Preparation of Lytic Composition

Component A: $Ca(OH)_2$ with the concentration of 0.1 mmol/L;
component B: PEG (with molecular weight of 100) with the concentration of 200 mg/mL;
a molar ratio of A to B is: 0.1:1.05;
the lytic composition is prepared.

Embodiment 3 Preparation of Lytic Composition

Component A: KOH with the concentration of 100 mmol/L;
component B: PEG (with molecular weight of 1000) with the concentration of 100 mg/mL;
a molar ratio of A to B is: 200:0.45;
the lytic composition is prepared.

Embodiment 4 Preparation of Lytic Composition

Component A: KOH with the concentration of 100 mmol/L;
component B: PEG (with molecular weight of 1000) with the concentration of 100 mg/mL;
reaction termination product: Turbo buffer.
a molar ratio of A to B is 100:0.8;
the lytic composition is prepared.

Embodiment 5 Preparation of Lytic Composition

Component A: KOH with the concentration of 50 mmol/L, thereby obtaining the composition.

Embodiment 6 Preparation of Lytic Composition

Component B: PEG (with molecular weight of 800) with the concentration of 50 mg/mL, thereby obtaining the composition.

Embodiment 7 Application of BRAF Gene Mutation Molecular Detection in Field of Molecular Diagnosis Human gene BRAFV600E is subjected to real-time fluorescent quantitative qPCR gene mutation detection by using the lytic composition prepared by Embodiment 4. Multiple human samples are directly subjected to the real-time quantitative qPCR by virtue of the lytic composition provided by the present invention, Including: (1) all reagents needed by the reaction, such as Taq enzymes, FAM fluorescent probes and forward and reverse primers, buffer, $Mg^{2+}$ and dNTPs; (2) negative control: (1 ng/μL) Hm gDNA; (3) 1-2 μL sample lytic composition; and (4) diluents: DNase-free Water.

The method for applying the reagents to BRAF gene mutation detection in the present invention has the characteristics of rapidness and convenience, is capable of directly carrying out qPCR without extracting the DNA, reducing contamination and reducing the amount of the samples; and since dual quality control points are set, the method is stable in detection results, suitable for standardization and high in throughput.

Experimental Procedures

Sample treatment (taking human intestinal tissues, esophageal tissues, urine and saliva as examples)
1. adding the lytic composition with a volume ratio of 1:(1-10) (V/V) prepared in the Embodiment 4 into the sample;
2. putting the centrifuge tube into a heating block at a temperature of 10-90° C. for about 25 minutes to 3 hours;
3. terminating the reaction: adding 200 μL of stop solution Turbo Buffer, centrifuging (10000 rpm, 2 min) after transient vortex, without purifying and extracting the nucleic acid, and taking 2 μL of coarse cell lysate as a template of a nucleic acid reaction below.

4. carrying out the qPCR (ABI7500 real-time fluorescent quantitative qPCR detection platform):

| Items | SS | Volume | Final Concentration |
|---|---|---|---|
| Real-Time qPCR Master Mix | TaqMan Master Mix (2×) including TaqMan enzymes, 4 kinds of dNTPs | 5 μL | 1× |
| BRAF forward primer | BRAF-f1 (18 μM) | 0.25 μL | 450 nmol/L |
| BRAF reverse primer | BRAF-r2 or -r1 (18 μM) | 0.25 μL | 450 nmol/L |
| BRAF probe | BRAF probe (4 μM) | 0.5 μL | 200 nmol/L |
| Template | DNAlysate above (sample) | 2 μL | 5-100 ng total |
| water | | 2 μL | |
| | final volume | 10 μL | | qPCR amplification genes: BRAF genes, qPCR amplification platform (ABI company): ABI 7500

Qpcr System:

| Items | Stock Solution | Volume | Final Concentration |
|---|---|---|---|
| Real-Time qPCR Master Mix | qPCRMaster Mix (2×) (dNTPs, enzymes)) | 10 μL | 1× |
| BRAF forward primer | BRAF-Fwd (18 μM) | 0.5 μL | 450 nmol/L |
| BRAF reverse primer | BRAF-RV (18 uM) | 0.5 μL | 450 nmol/L |
| BRAF probe | BRAF probe (4 μM) | 1 μL | 200 nmol/L |
| Template | Sample | 2 μL | 5-100 ng total |
| Water | | 6 μL | |
| Final Volume | | 20 μL | |

For BRAF gene probe, primer sequence is as follows:

| | Sequence | Oligo Nmae | 5' mod | Seq 5'→3' | 3' mod |
|---|---|---|---|---|---|
| 1 | As shown in seq ID No. 1 | BRAF-asp-600Glu-rv1 | none | CCCACTCCATCGAGATTTCT | none |
| 2 | As shown in seq ID No. 2 | BRAF-reference-rv2 | none | CAACTGTTCAAACTGATGGG | none |
| 3 | As shown in seq ID No. 3 | BRAF-fwd1 | none | CTGTTTTCCTTTACTTACTACACCTCAGAT | MGB |
| 4 | As shown in seq ID No. 4 | BRAF-probe | FAM | FAM-CACAGTAAAAATAGGTGAT-MGB | MGB |

III. qPCR Procedures (Pikoreal Detection Platform)

| Temperature | Time | Cycle number | Description |
|---|---|---|---|
| 95° C. | 10 min | 1 cycle | Pre-degeneration |
| 95° C. | 15 s | 45 cycles | Degeneration/ annealing extension |
| 58° C. | 1 min | | |
| Data aquisition | | | |
| 20° C. | 10 s | / | Termination |

Figure 1:
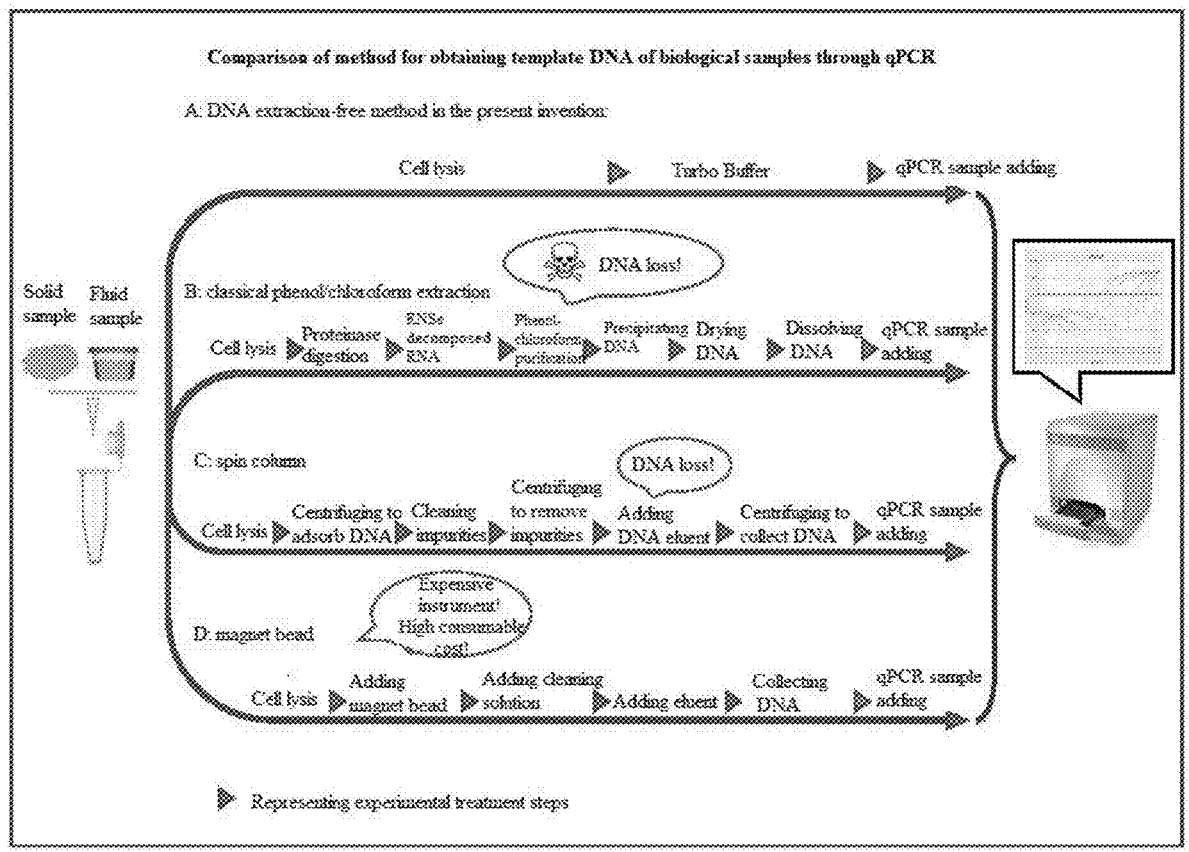
FIG. 1 illustrates comparison of a method for preparing nucleic acid by using a lytic composition provided by the present invention and a conventional method.
Figure 2:
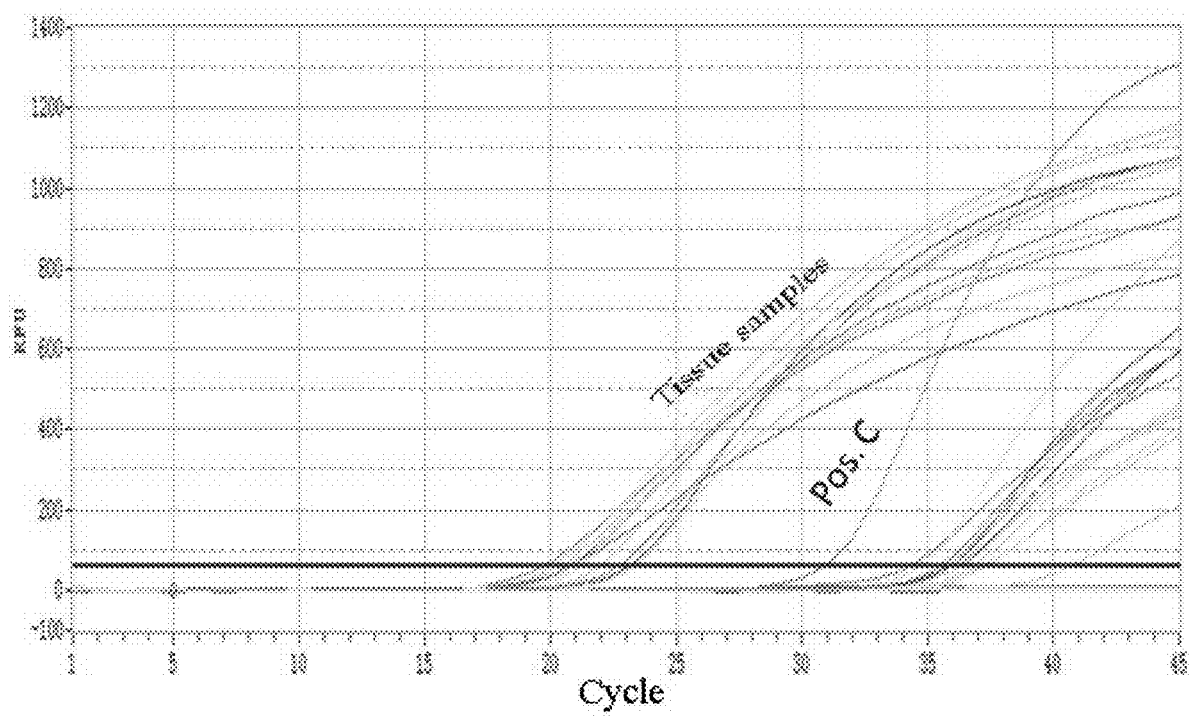
FIG. 2 is a diagram illustrating a real-time fluorescent quantitative PCR (qPCR) method for performing molecular amplification of detecting BRAF gene mutation, wherein, a tissue sample 1 refers to operative intestinal polyp and cancer tissues (taken from First Affiliated Hospital of Guizhou Hospital of Traditional Chinese Medicine), a tissue (sample 2) refers to operative esophageal carcinoma tissues (taken from First Affiliated Hospital of Suzhou University), tissue #3 refers to blocks of hydrothorax tissue (taken from Fuzhou General Hospital of Nanjing Military), #4 and #5 refer to two independent normal persons, NTC (taking water as template-free negative control), and Pos.C is gDNA of positive control. gDNA (human genome DNA) refers to human genome DNA (a product of Company Roche) purified and extracted by the conventional method, serving as a DNA template; in all the experimental examples of this article, the gDNA purified and extracted by the conventional method serves as the positive control so as to compare with positive control of a DNA mixture without extraction and purification by the method provided by the present invention)

See FIG. 2 for detection results (pikoreal detection platform).

The BRAFgene mutation detection method in the present invention has the characteristics of rapidness and convenience, is capable of directly carrying out qPCR without extracting the DNA, reducing the contamination and reducing the amount of the samples; and since the dual quality control points are set, the method is stable in detection results, suitable for standardization and high in throughput.

Embodiment 8 BRAFgene Amplification

Sample treatment method: the same as that in Embodiment 7;

qPCR Procedures:

| 95° C. | 10 min | |
|---|---|---|
| 95° C. | 15 sec | |
| 58° C. | 1 min | } 45 cycles; |
| 4° C. | 2 min | |

1. Colon Cancer Tissues and Lung Cancer Hydrothorax Tissue Blocks

Source of lung cancer hydrothorax tissue blocks: Fuzhou General Hospital of Nanjing Military. There are macroscopic tissue blocks (adenocarcinoma cells) in the samples. Source of colon cancer tissues: First Affiliated Hospital of Guiyang Hospital of Traditional Chinese Medicine. The samples are excisional tissues.

See descriptions of sample tissue treatment methods in Embodiment 7 for solid sample treatment methods. The other conditions are the same as above, wherein the curve 1 illustrates intestine tissue-Endo-ref; the curve 2 illustrates gDNA-Endo-ref-neg.C (20 ng); the curve 3 illustrates hydrothorax tissue block-Endo-ref; the curve 4 illustrates intestine tissue-Mut; the curve 5 illustrates gDNA-Mut-neg.C (20 ng); and the curve 6 illustrates hydrothorax tissue-Mut.

[Remarks: gDNA: human genome DNA, coming from (the product of Roche) the experimental control by using the conventional DNA extraction and purification method, Endo=endogenous DNA (endogenous DNA), Ref=reference (reference), Mut=mutation (mutant), C=Control (control)]

| Primer | Sequence | Cq |
|---|---|---|
| BRAF-ref (RV2) | NTC | Non-numeric |
| | 20 ng gDNA | 25.44 |
| | 101# hydrothorax block | 28.45 |
| | 103# intestine tissue block | 23.09 |
| BRAF-mut (RAV1) | NTC | Non-numeric |
| | 20 ng gDNA | 34.6 |
| | 101# hydrothorax block | 39.68 |
| | 103# intestine tissue block | 33.87 |

Figure 3:
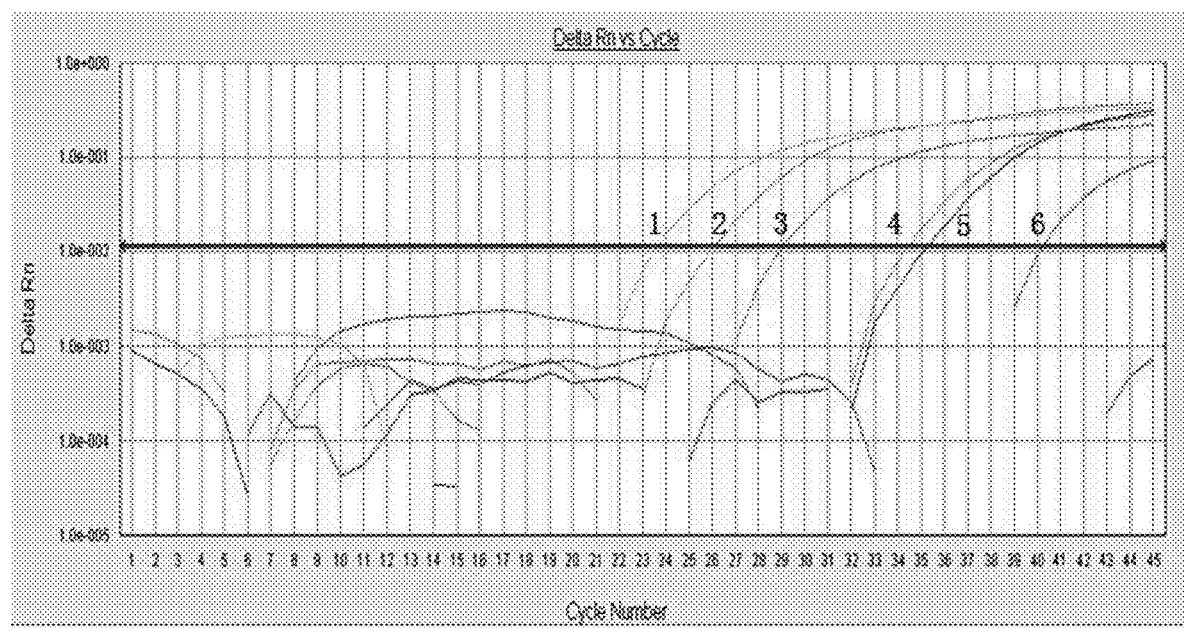
FIG. 3 is a diagram illustrating BRAF gene qPCR amplification of colonic carcinoma tissues and lung cancer hydrothorax tissue blocks in Embodiment 8. In amplification curves from the left to the right, #1: Endoref of intestinal polyp tissues of the sample 1; #2: gDNA positive control; #3: the sample 3 (hydrothorax tissue blocks), the fourth and fifth curves illustrate urine and saliva, and the curve 6 refers to BRAF mutation detection by using the sample 1 (not a mutant shown). There is no amplification curve in the NTC (taking water as template-free negative control).

See FIG. 3 for result analysis (ABI7500 platform).
ΔCt=Mut (sample)−Endo-ref (sample)
Negative control (neg. C) ΔCt=9.16
Intestine tissue sample ΔCt=10.78>8.5(ΔCt>8.5 is setting of kit cut off on non-mutant)
Hydrothorax tissue block sample ΔCt=11.23>8.5(ΔCt>8.5 is setting of kit cut off on non-mutant)

Therefore, the two samples are wild-type BRAF mutation negative samples.

Conclusion the BRAF mutation detection kit is capable of conveniently and rapidly detecting multiple types of clinical tissue samples on ABI7500 platform, and is high in specificity and sensitivity.

2. Esophageal Carcinoma Tissues and Colon Polyp Tissues

Sample Source:

Source of esophageal carcinoma tissues: First Affiliated Hospital of Suzhou University; and source of colon polyp tissues (different from the tissues above): First Affiliated Hospital of Guiyang Hospital of Traditional Chinese Medicine.

The other conditions are the same as above.

Figure 4:
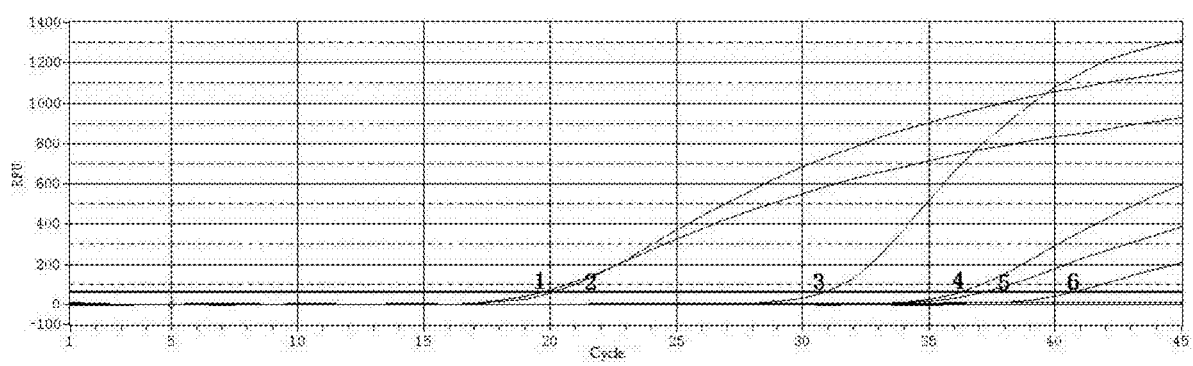
FIG. 4 is a diagram illustrating BRAF gene qPCR amplification of esophageal carcinoma tissues and colon polyp tissues in Embodiment 8, wherein a curve 1 illustrates intestine tissue-Endo-ref; a curve 2 illustrates esophageal tissue-Endo-ref; a curve 3 illustrates gDNA neg.C (1 ng); a curve 4 illustrates esophageal tissue-Mut; a curve 5 illustrates intestine tissue-Mut; and a curve 6 illustrates gDNA neg.C (1 ng)-Mut.

See FIG. 4 for qPCR result (ABI Picoreal platform), wherein the curve 1 illustrates intestine tissue-Endo-ref; the curve 2 illustrates esophageal tissue-Endo-ref; the curve 3 illustrates gDNA neg.C (1 ng); the curve 4 illustrates esophageal tissue-Mut; the curve 5 illustrates intestine tissue-Mut; and the curve 6 illustrates gDNA neg.C (1 ng)-Mut.

| Primer | Sample | Cq |
|---|---|---|
| rv2 (ref) | NTC | Non-numeric |
| | 1 ng gDNA(neg C) | 30.84 |
| | Intestine tissue block | 19.65 |
| | Esophageal tissue | 20.13 |
| rv1 (mut) | NTC | Non-numeric |
| | 1 ng gDNA | 40.63 |
| | Intestine tissue block | 37.11 |
| | Esophageal tissue | 36.23 |

Result: ΔCt=Mut (sample)−Endoref (sample)
Negative control (neg. C) ΔCt=9.79
Intestine tissue sample ΔCt=17.46>8.5(>8.5 is cut off setting of kit on mutant)
Esophageal tissue sample ΔCt=16.1>8.5(>8.5 is cut off setting of kit on mutant)
Therefore, the two samples are BRAF mutation negative samples.
Conclusion: the BRAF mutation detection kit is capable of conveniently and rapidly detecting various types of clinical tissue samples on Pikoreal platform, and is high in specificity and sensitivity.

3. Application of Gastric Juice and Sputum for Performing BRAF Gene qPCR Amplification and Detection Point Mutation:

Fluid sample treatment methods are the same as descriptions of IL28 SNPs fluid sample tissue treatment methods in Embodiment 9 and Embodiment 10.

The other conditions are the same as above.

Figure 5:
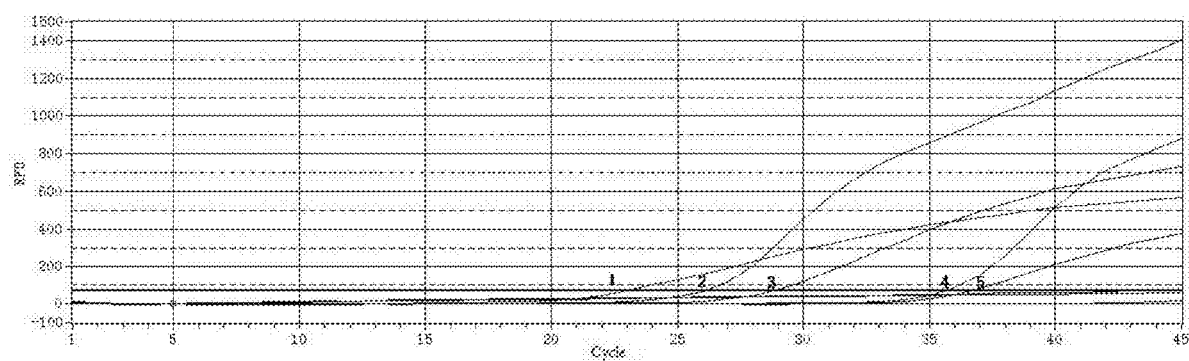
FIG. 5 is a diagram illustrating BRAF gene qPCR amplification of gastric juice and sputum in Embodiment 8, wherein a line 1 illustrates the sputum: Endo-ref (endogenous reference); a line 2 illustrates gDNA (20 ng): Endo-ref-C (endogenous reference); a line 3 illustrates gastric juice: Endo-ref (endogenous reference); a line 4 illustrates gDNA (20 ng): Mut-neg-C (mutantnegative control); and a line 5 illustrates sputum: Mut (mutation detection, sample is BRAF wild type, that is, mutant negative)

See FIG. 5 for experimental results (ABI Pikoreal platform).
The line 1 illustrates sputum: Endo-ref (endogenous reference)
The line 2 illustrates gDNA* (20 ng): Endo-ref-C (endogenous reference)
The line 3 illustrates gastric juice: Endo-ref (endogenous reference)
The line 4 illustrates gDNA* (20 ng): Mut-neg-C (mutant-negative control).
The line 5 illustrates sputum: Mut (mutation detection, sample is BRAF wild type, i.e., mutant negative)

The results above show that samples #1-5 are subjected to qPCR amplification and results of #4 and 5 on BRAF point mutation detection are: BRAF mutation detection results of #5 sample show that the sputum sample is of a BRAF wild type.

| Target gene | Template | Cq | RFU |
|---|---|---|---|
| BRAF-ref (reference) | NTC | Non-numeric | 67.39 |
| | 20 ng gDNA* | 26.11 | 1403.91 |
| | Gastric juice | 28.79 | 730.4 |
| | Sputum | 22.94 | 567.14 |
| BRAF-mut | NTC | Non-numeric | 56.92 |
| | 20 ng gDNA* | 35.59 | 881.23 |
| | Gastric juice | Non-numeric | 18.98 |
| | Sputum | 36.65 | 374.36 |

Conclusion:
the BRAF mutation detection kit is capable of conveniently and rapidly detecting multiple types of clinical tissue samples on the ABI7500 platform, and is high in specificity and sensitivity.

4. Application of Blood, Saliva and Urine for Performing BRAF Gene qPCR Amplification and Mutation Detection Blood, saliva and urine treatment methods are the same as descriptions of the IL28 SNPs fluid sample tissue treatment methods in Embodiment 9 and Embodiment 10.

Figure 6:
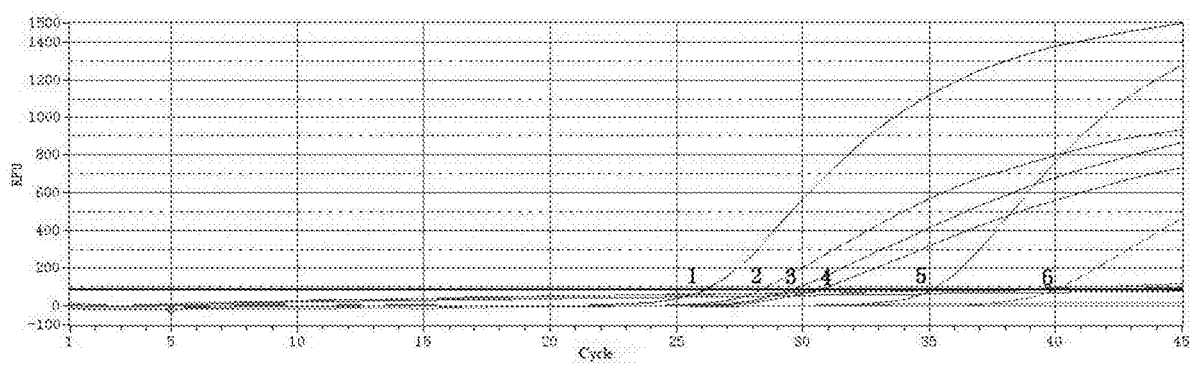
FIG. 6 is a diagram illustrating BRAF gene qPCR amplification of blood, saliva and urine, wherein a curve 1 illustrates gDNA: Endoref-neg.C (20 ng) (human genome DNA endogenous reference, BRAF mutant negative control); a curve 2 illustrates blood-Endo-ref (endogenous reference); a curve 3 illustrates saliva-Endo-ref (endogenous reference); a curve 4 illustrates urine-Endo-ref (endogenous reference); a curve 5 illustrates gDNA: Mut-neg.C (20 ng) (human genome DNABRAF mutation detection-negative control); and a curve 6 illustrates blood: Mut (mutant detection)

The other conditions are the same as above. See FIG. 6, wherein the curve 1 illustrates gDNA-Endo-ref-neg.C (20 ng) (human genome DNA endogenous reference, BRAF negative control); the curve 2 illustrates blood-Endo-ref (endogenous reference); the curve 3 illustrates saliva-Endo-ref (endogenous reference); the curve 4 illustrates urine-Endo-ref (endogenous reference); the curve 5 illustrates gDNA-Mut-neg.C (20 ng) (human genome DNA BRAF mutation detection-negative control); and the curve 6 illustrates blood:Mut (mutant detection) (Blood BRAF mutation detection results show that the sample is of a BRAF wild type. A ratio of causing cancers by BRAF mutants is low in China.)

Conclusion:
the BRAF mutation detection kit is capable of conveniently and rapidly detecting multiple types of the clinical tissue samples, and is high in specificity and sensitivity.

| Target gene | Template | Cq | RFU |
|---|---|---|---|
| BRAF-ref | NTC | Non-numeric | 17.76 |
| | 20 ng gDNA | 26.13 | 1496.04 |
| | Saliva | 29.59 | 863.87 |
| | Urine | 30.55 | 733.9 |

| Target gene | Template | Cq | RFU |
|---|---|---|---|
| | Blood | 28.32 | 930.68 |
| BRAF-mut | NTC | Non-numeric | 79.64 |
| | 20 ng gDNA | 35.13 | 1278.79 |
| | Saliva | 38.4 | 115.72 |
| | Urine | 40.4 | 97.18 |
| | Blood | 39.96 | 463.87 |

5. Hydrothorax BRAF Gene qPCR Amplification and Mutation Detection Results

Figure 7:
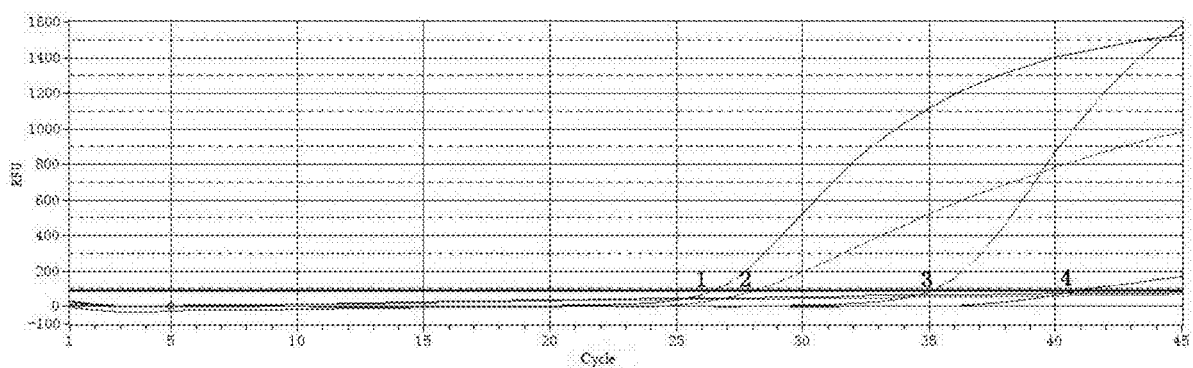
FIG. 7 is a diagram illustrating BRAF gene qPCR amplification of hydrothorax in Embodiment 8, wherein a curve 1 illustrates gDNA-Endo-ref-neg.C (20 ng) (human genome DNA endogenous reference, BRAF negative control); a curve 2 illustrates hydrothorax-Endo-ref (endogenous reference); a curve 3 illustrates gDNA-Mut-neg.C (20 ng) (human genome DNABRAF mutation detection-negative control); and a curve 4 illustrates hydrothorax-Mut (mutant detection).

Hydrothorax collected samples are taken from Fuzhou General Hospital of Nanjing Military, and there are macroscopic tissue blocks and liquid in the samples. See the descriptions of the IL28 SNPs fluid sample tissue treatment methods for sample treatment methods. The other conditions are the same as above. See FIG. 7, wherein the curve 1 illustrates gDNA-Endo-ref-neg.C (20 ng) (human genome DNA endogenous reference, BRAF negative control); the curve 2 illustrates hydrothorax-Endo-ref (endogenous reference); the curve 3 illustrates gDNA-Mut-neg.C (20 ng) (human genome DNABRAF mutation detection-negative control); and the curve 4 illustrates hydrothorax-Mut (mutation detection).

Detection Results:

| Target gene | Target gene | Cq | RFU |
|---|---|---|---|
| BRAF-ref | NTC | Non-numeric | 66.83 |
| (Reference) | 20 ng gDNA | 26.33 | 1528.8 |
| | Hydrothorax | 27.99 | 981.75 |
| BRAF-mut | NTC | Non-numeric | 82.01 |
| (mutation | 20 ng gDNA | 35.02 | 1579.33 |
| test) | Hydrothorax | 40.76 | 169.68 |

Conclusion:

the mutation detection kit in the present invention is capable of conveniently and rapidly detecting multiple types of the clinical tissue samples on the ABIPicoreal platform, and is high in specificity and sensitivity.

Taking the experiments above together, the detection results show that the human samples can be amplified by using the qPCR method, and all the samples are of the wild type, instead of a mutant type. Solid samples contain more DNA than fluid samples, so an amplification rate is higher (cn value keeping to the left is smaller); and the lysed mixed solution without extracting DNA in the present invention and purified gDNA control have the same result (circle number=23) (circle number is in a range of 22-32, within cut-off=35).

The BRAF gene mutation detection method in the present invention has the characteristics of rapidness and convenience, is capable of directly carrying out qPCR without extracting the DNA, reducing the contamination and reducing the amount of the samples; and since the dual quality control points are set, the method is stable in detection results, suitable for standardization and high in throughput.

Embodiment 9 SNP-IL28B-a of Saliva (Detection of SNPs Polymorphism by Real-Time Fluorescent Quantitative qPCR)

1. adding 10 μL of saliva sample into a 1.5 ml centrifuge tube, and adding the lytic composition prepared in Embodiment 1 according to a ratio of 1:1;

2. putting the centrifuge tube into vortex for 10 s, and centrifuging at 5K rpm for 1 minute;

3. putting the centrifuge tube into the heating block at a temperature of 30-90° C., and standing for about 30 minutes to 2 hours;

4. adding 20 μL HH of Turbo Buffer, keeping in the vortex for 10 s, and centrifuging at 10K rpm for 2 minutes;

5. taking 2 μL of supernatant in the centrifuge tube, and adding into 8 connected tubes or 96 well plates for carrying out double-probe real-time fluorescent quantitative qPCR.

SNPs qPCR system: (taking a 20 μL reaction system as an example)

| Items | Volume |
|---|---|
| Real-Time qPCR master mix | 10 μL |
| IL28B SNPs forward primer | 0.5 μL |
| IL28B SNPs reverse pimer | 0.5 μL |
| IL28B SNPs pobe FAM | 1 μL |
| IL28B SNPs probe HEX | 1 μL |
| Template | 2 μL |
| Water | to 20 μL |

Qpcr Process:
1. Pre-read AD (Allelic Discrimination)
2. Amplification AQ (Absolute Quantification)

| | | |
|---|---|---|
| 50° C. | 2 min | 1 cycle |
| 95° C. | 10 min | } 45 cycles |
| 95° C. | 15 s | |
| 60° C. | 1 min | |

3. Post-Read AD (Allelic Discrimination)

Figure 8:
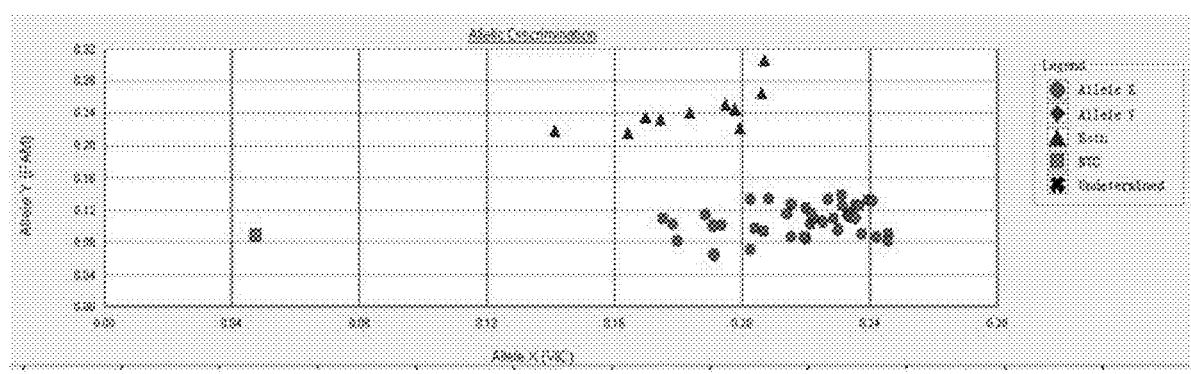
FIG. 8 is a diagram illustrating IL28B-site a allelic discrimination (SNP), wherein in a green group, dots illustrate CC homozygote type; in a red group, triangles illustrate T heterozygote type; there is no amplification at a position close to the origin (square) of template-free control, and positive control gDNA is CT heterozygote type (red triangle)

Taking Applied BioSystems 7500 as an example (IL28B-a), as shown in FIG. 8.

The detection results show that the human samples can be amplified by using the qPCR method so as to detect SNPs, and the samples include the CC homozygote type (green group, dots), and the CT heterozygote type (red group, red triangle), without the TT type. There is no amplification at a position close to the origin (square) of the template-free control, and positive control gDNA is the CT heterozygote type (red triangle). The results show that the lysed mixed solution without extracting the DNA in the present invention is successful in genetic typing, and has consistent amplification and typing results with the purified gDNA control.

Embodiment 10 Gene Polymorphism qPCR Analysis-IL28B SNPs

The same sample is treated in the presence or absence of the lysate, and IL28B gene amplification and typing conditions are compared by using Realtime qPCR.

Experimental Process:
(I) Saliva Sample Treatment:

1. Keeping sample stock solution (containing a stabilizer) in a saliva sample tube 1 in vortex for 10 s, centrifuging at 10K rpm for 2 minutes, and taking 20 μL of the supernatant into a new centrifuge tube 2, wherein the sample stock solution in the tube 1 is for later use;

2. #2 tube: adding the lysate prepared in Embodiment 2: adding 20 μL of the lysate into the tube 2, keeping in vortex for 5 s, and centrifuging at 5K rpm for 1 minute; standing at a temperature of higher than 30° C. for 1 hour, and keeping in vortex twice; after standing, keeping in vortex for 5 s, centrifuging at 10K rpm for 2 minutes, and taking 20 μL of the supernatant into a new centrifuge tube 3, wherein the lysate in the tube 2 is for later use; 3. tube 3, adding the lysate prepared in Embodiment 2 and Turbo buffer: adding 20 μL of Turbo buffer into the tube 3, keeping in vortex for 5 s, and centrifuging at 10K rpm for 2 minutes, wherein the treated lysate+Turbo buffer in the tube 3 is for later use.

Notes: tube 1: without lysate(−lysate)
tube 2: with lysate(+lysate)
tube 3: with lysate+Turbo buffer(+lysate+Turbo buffer)

(II) SNPs Typing qPCR System

| Items | Volume |
| --- | --- |
| Real-Time qPCR Master Mix | 5 μL |
| IL28B SNPs forward primer | 0.25 μL |
| IL28B SNPs reverse primer | 0.25 μL |
| IL28B probe T | 0.5 μL |
| IL28B Probe C | 0.5 μL |
| Template | 2 μL |
| water | 1.5 μL |
| final volume | 10 μL |

(III) qPCR Process

| Temperature | Time | Cycle number |
| --- | --- | --- |
| 25° C. Data acquisition | 30 s | |
| 95° C. | 10 min | 1 cycle |
| 95° C. | 15 s | 45 cycles |
| 62° C. Data aquisition | 1 min | |
| 30° C. | 10 s | |
| 25° C. Data aquisition | 30 s | |

IL28B Gene SNP Probe, Primer Sequence:

| | Sequence | Oligo Nmae | 5' mod | Seq 5'→3' | 3' mod |
| --- | --- | --- | --- | --- | --- |
| 1 | As shown in seq ID No. 5 | IL28B-rs12979860-fwd | none | TGTACTGAACC AGGGAGCTC | none |
| 2 | As shown in seq ID No. 6 | IL28B-rs12979860-rv | none | GCGCGGAGTGC AATTCAAC | none |
| 3 | As shown in seq ID No. 7 | IL28B-rs12979860-probeT | FAM | FAM-CTGGTTCA CGCCTTC-MGB | MGB |
| 4 | As shown in seq ID No. 8 | IL28B-rs12979860-probeC | HEX | HEX-TGGTTCGC GCCTTC-MGB | MGB |

See SNPs result analysis (target gene IL28B—site a) in Table 1.

TABLE 1

| | | SNPs result analysis | | | |
| --- | --- | --- | --- | --- | --- |
| No. | Sample | RFU1 = FAM | RFU2 = HEX | HEX: FAM | Reesult |
| 1 | NTC | −3.89 | 26.44 | | − |
| 2 | gDNA (CTgenotype control) | 1092.48 | 2742.1 | 2.51 | + |
| 3 | Untreated sample stock solution (tube 1) | 308.84 | 392.9 | 1.27 | − |
| 4 | Sample treated by lysate (tube 2) | 769.84 | 1869.4 | 2.43 | + |
| 5 | Sample treated by + Turbo buffer(tube 3) | 543.21 | 2101.08 | 3.87 | + |

Figure 9:
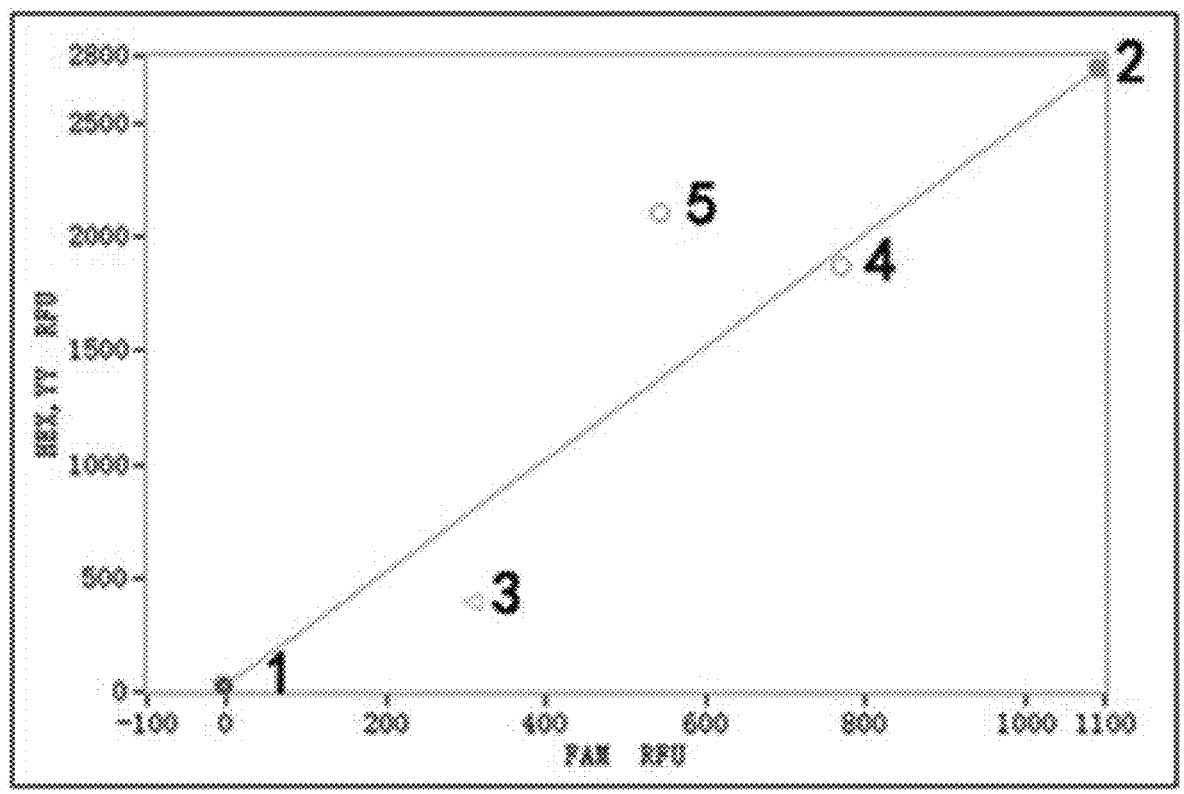
FIG. 9 is a diagram illustrating IL28B-site a allelic discrimination (SNP) by using a real-time fluorescent quantitative qPCR method, wherein a sequence number 1 represents NTC, that is, template-free control; 2 represents gDNA CT Control, that is, heterozygote (CT type) control; 3 represents untreated sample stock solution, that is, negative control; 4 represents a sample treated in lysate, that is, an experimental sample; and 5 represents a sample treated in lysate and Turbo buffer, that is an experimental test sample.

See FIG. 9 for results, wherein the curve 1 illustrates NTC, i.e., template-free control; the curve 2 illustrates gDNA (CT type), i.e., known heterozygote control; the curve 3 illustrates the untreated sample stock solution, serving as an experimental sample; the curve 4 illustrates the sample treated by lysate, serving as the experimental sample; and the curve 5 illustrates the sample treated by lysate+Turbo buffer, serving as an experimental testing sample.

Note: IL28B a includes types CC, CT and TT.

Descriptions of IL28B—Site Allelic Discrimination Diagram:

1. According to CT type (No. 2) heterozygote control data of gDNA IL28B-apolymorphism, the sample is a CT heterozygous genotype of IL28B—site a.

2. Whether the sample is treated by the lysate or not is compared, and the sample stock solution which is not treated by the lysate (No. 3) is positioned at a gray point close to the origin in the figure; it shows that the sample is not amplified or subjected to fewer amplification, and is beyond a set value of a numerical value (cut-off) which can be accepted by polymorphic analysis.

3. For the sample treated by lysate (No. 4) and the sample treated by lysate and Turbo buffer (No. 5), absolute values of an FAM channel and an HEX channel are obviously increased, and the sample treated by the lysate has a good fluorescent quantitative qPCR amplification effect.

4. According to fluorescent quantitative qPCR amplification comparison: "the sample treated by the lysate and Turbo buffer" (No. 5) is superior to "the sample treated by the lysate" (No. 4)".

Embodiment 11 Direct Use of Cell Lysate in Ordinary PCR Amplification without DNA Extraction Effects of cell lysate (A+B) in PCR experiments are verified, DNA extraction is avoided, and the lysate is directly used in the PCR experiments.

Experimental Design:
Experimental samples: fluid samples-cryopreserved blood samples; solid samples-cryopreserved human esophageal biopsy tissues Sample Treatment:
(I): blood
Adding 10 μL of blood and 90 μL of water, gently shaking and uniformly mixing, centrifuging at 5K rpm for 5 minutes; removing the supernatant, adding 10 μL of precipitate and 100 μL of water, gently shaking and uniformly mixing, and centrifuging at 5K rpm for 5 minutes; removing the supernatant, and taking 10 μL of precipitate:

A: Negative Control:
adding 10 μL of precipitate and 10 μL of ddH$_2$O, treating at the temperature of 30-90° C. for an hour, and then adding 20 μL of ddH$_2$O;

B: Samples+Lysate:
adding 10 μL of precipitate and 10 μL of lysate prepared in Embodiment 5, treating at a temperature of more than 30° C. for an hour, and taking out 104, of liquid;

C: Samples+Lysate Prepared in Embodiment 5+Turbo Buffer:
adding 10 μL of precipitate and 10 μL of Turbo Buffer, treating at the temperature of 30-90° C. for over 30 minutes, keeping in vortex for 5 s, centrifuging at 10K rpm for 2 minutes for later use;

(II) Human Esophageal Tissues:
Respectively Weighing the Esophageal Tissues

D: Negative Control:
Adding 30 mg+10 μL of ddH$_2$O, treating at the temperature of more than 30-90° C. for over 30 minutes, +604, of H2O

E: Sample Solution+Lysate:
30 mg+804, of lysate prepared in Embodiment 6, 30-90° C., over 30 minutes, taking out 604, of lysate

F: Sample+Lysate+Turbo Buffer:
like #5, 204, of lysate prepared in Embodiment 6+200 μL of Turbo buffer, keeping in vortex for 5 s, and centrifuging at 10K rpm for 2 minutes;

PCRenzyme: Taq PCR SuperMix
Amplified genes: BRAF
PCR Amplification System:

| Items | Volume | Final concentration |
|---|---|---|
| Template | 2 μL | |
| Braf forward primer | 0.83 μL | 300 nM |
| Braf reverse primer | 0.83 μL | 300 nM |
| 2 × PCR supermix | 25 μL | 1× |
| Water | 21.34 μL | |
| Total | 50 μL | |

PCR Amplification Procedure:

| | | |
|---|---|---|
| 95° C. | 5 min | |
| 95° C. | 15 sec | |
| 55° C. | 15 sec | 45 cycles |
| 72° C. | 30 sec | |
| 72° C. | 10 min | |
| 4° C. | — | |

Electrophoresis parameter: 70 v 90 min
3% agarose gel
TAE buffer
Nucleic acid dyes: GeneFinder
BRAF Gene Primer:

| Sequence | oligo name | seq 5'→3' |
|---|---|---|
| 1 As show in seq ID No. 2 | BRAF-rv1 | CAACTGTTCAAACTGATGGG |
| 2 As show in seq ID No. 3 | BRAF-fwd1 | CTGTTTCCTTTACTTACTACACCTCAGT |

See FIG. 10 for experimental results.
The templates are sequentially as follows from the left lane to the right lane
qPCR Result (about 110 bp-Amplified Fragments)

| | |
|---|---|
| NTC (template-free control) | − |
| 20 ng gDNA (human genome DNA control) | + |
| Blood (−lysate) | − |
| Blood (+lysate) | + |
| Blood (+lysate + Turbo buffer) | + |
| Esopagus (−lysate) | − |
| Esopagus (+lysate) | + |
| Esopagus (+lysate + Turbo buffer) | + |

Note:
the human genome DNA is DNA control extracted and purified by the conventional method.

Experiment Conclusion:
By using the lysate (AB+C) in the present invention, the human fluid and solid samples can be directly subjected to ordinary PCR amplification without extracting the DNA. The descriptions above are only preferred embodiments of the present invention. It should be indicated that, those ordinary skilled in the art may carry out several improvements and modifications on the premise of not deviating from the principle of the present invention, and these improvements and modifications can also be considered as the protection scope of the present invention.

What is claimed is:

1. A lytic composition, wherein the composition is formed by combining A component and B component, A is Ca(OH)$_2$, and B is PEG with a molecular weight of 100; the concentration of A is 0.1 mmol/L, and the concentration of B is 200 mg/mL; a molar ratio of A to B is 0.1:1.05; and the lytic composition further comprises a reaction termination product.

2. A method of preparing nucleic acid, comprising:
lysing a biological sample using a lytic composition comprising A component and B component at 30-90° C. for 10 minutes to 8 hours; and
adding a reaction termination product to terminate reaction and centrifuging the reaction product to produce the nucleic acid;
wherein A is Ca(OH)$_2$, and B is PEG with a molecular weight of 100;
the concentration of A is 0.1 mmol/mL, and the concentration of B is 200 mg/mL; a molar ratio of A to B is 0.1:1.05;
the weight (g)-volume (mL) ratio the biological sample to the lytic composition comprising A component and B component is 1: 1-1:10;
and the resulting nucleic acid is directly used for nucleic acid amplification or nucleic acid analysis without purification.

3. The method of claim 2, wherein the nucleic acid analysis comprises an amplified reaction, mutant site detection or SNPs detection.

4. The method of claim 2, wherein the nucleic acid analysis is selected from a reverse transcription polymerase chain reaction (PCR), a ligase-chain reaction (LCR), a gap-LCR, a repaired chain reaction, transcription-mediated amplification, autonomous sequence replication, selective amplification of target polynucleotide series, a consensus sequence primer PCR, a random primer PCR, nucleic acid sequence based amplification, strand displacement amplification, loop-mediated isothermal amplification, DNA methylation a DNA ligation reaction and a nuclease-mediated reaction.

5. The method of claim 4, wherein the PCR is a quantitative polymerase chain reaction (qPCR) comprising DNA and RNA or a reverse transcription qPCR comprising DNA and RNA.

6. The method of claim 5, wherein the reverse transcription qPCR comprises ordinary RNA reverse transcription and RNAi reverse transcription.

7. The method of claim 2, wherein the biological sample is selected from animal cells, animal tissues, human cells and human tissues.

8. The method of claim 7, wherein the human tissues or animal tissues comprise fluid tissues and solid tissues.

9. The method of claim 8, wherein the fluid tissues are selected from one or more of-saliva, sputum, throat fluid, esophagus (sputum) fluid, urine, blood, gastric juice, hydrothorax, pulmonary edema, hydrohepatosis, abdominal dropsy, vaginal discharge fluid, uterine drain fluid, sweat, parotid gland cells, lymph, marrow fluid, milk, tears, seminal fluid, spinal fluid, brain marrow, amniotic fluid, synovial fluid, nasal discharge or nasal excrements.

10. The method claim 8, wherein the solid tissue is selected from one or more of intestinal tissues, throat tissues, esophageal tissues, bladder tissues, abdominal tissues, tumor tissues, cell lines, lung tissues, hepatic tissues, gastric tissues, nephridial tissues, pancreatic tissues, prostate tissues, uterus tissues, vaginal tissues, ovarian tissues, gall tissues, heart tissues, dermal tissues, brain, tumors, fingernails, hair on the human body and head, hair follicles, intestinal excretion tissues or excrements.

11. A kit, wherein the kit comprises the lytic composition of claim 1.

* * * * *

SEQUENCE LISTING

<160> NUMBER OF SEQ ID NOS: 8

<210> SEQ ID NO 1

```
<211> LENGTH: 20
<212> TYPE: DNA
<213> ORGANISM: Artificial Sequence
<220> FEATURE:
<223> OTHER INFORMATION: synthetic

<400> SEQUENCE: 1
cccactccat cgagatttct                                                    20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
caactgttca aactgatggg                                                    20

<210> SEQ ID NO 3
<211> LENGTH: 30
<212> TYPE: DNA
<213> ORGANISM: Artificial Sequence
<220> FEATURE:
<223> OTHER INFORMATION: synthetic

<400> SEQUENCE: 3
ctgttttcct ttacttacta cacctcagat                                         30

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
cacagtaaaa ataggtgat                                                     19

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
tgtactgaac cagggagctc                                                    20

<210> SEQ ID NO 6
<211> LENGTH: 19
<212> TYPE: DNA
<213> ORGANISM: Artificial Sequence
<220> FEATURE:
<223> OTHER INFORMATION: synthetic

<400> SEQUENCE: 6
gcgcggagtg caattcaac                                                     19

<210> SEQ ID NO 7
<211> LENGTH: 15
<212> TYPE: DNA
<213> ORGANISM: Artificial Sequence
<220> FEATURE:
<223> OTHER INFORMATION: synthetic

<400> SEQUENCE: 7
```

```
ctggttcacg ccttc                                                    15
```

<210> SEQ ID NO 8
<211> LENGTH: 14
<212> TYPE: DNA
<213> ORGANISM: Artificial Sequence
<220> FEATURE:
<223> OTHER INFORMATION: synthetic

<400> SEQUENCE: 8

```
tggttcgcgc cttc                                                     14
```